United States Patent
Blease et al.

(10) Patent No.: US 9,681,658 B2
(45) Date of Patent: Jun. 20, 2017

(54) PENETRANTS FOR AGROCHEMICAL FORMULATIONS

(71) Applicant: CRODA INTERNATIONAL PLC, Yorkshire (GB)

(72) Inventors: Trevor Graham Blease, Cleveland (GB); Kathryn Marie Knight, Yorkshire (GB)

(73) Assignee: Croda International PLC, East Yorkshire (GB)

( * ) Notice: Subject to any disclaimer, the term of this patent is extended or adjusted under 35 U.S.C. 154(b) by 0 days.

(21) Appl. No.: 14/443,865

(22) PCT Filed: Nov. 19, 2013

(86) PCT No.: PCT/GB2013/053043
§ 371 (c)(1),
(2) Date: May 19, 2015

(87) PCT Pub. No.: WO2014/080190
PCT Pub. Date: May 30, 2014

(65) Prior Publication Data
US 2015/0289502 A1   Oct. 15, 2015

(30) Foreign Application Priority Data
Nov. 20, 2012   (GB) .................................. 1220886.4

(51) Int. Cl.
*A61K 31/4168*   (2006.01)
*A01N 25/00*   (2006.01)
*A01N 25/30*   (2006.01)
*C08G 63/78*   (2006.01)

(52) U.S. Cl.
CPC ............. *A01N 25/00* (2013.01); *A01N 25/30* (2013.01); *C08G 63/78* (2013.01)

(58) Field of Classification Search
CPC .......................... A61K 31/44; A61K 31/4168
USPC ........................................................ 514/341
See application file for complete search history.

(56) References Cited

U.S. PATENT DOCUMENTS

| 7,521,397 B2 | 4/2009 | Dunkel |
| 2004/0171492 A1 | 9/2004 | Mainx |
| 2008/0312290 A1 | 12/2008 | Vermeer |
| 2009/0247597 A1 | 10/2009 | Vermeer |
| 2010/0041710 A1 | 2/2010 | Baur |

FOREIGN PATENT DOCUMENTS

| WO | 9400508 | | 1/1994 |
| WO | 9616930 | | 6/1996 |
| WO | 03003830 | | 1/2003 |
| WO | 03070705 | | 8/2003 |
| WO | 2004016088 | | 2/2004 |
| WO | 2005059042 | | 6/2005 |
| WO | 2010072341 | | 7/2010 |
| WO | WO-2010072341 | * | 7/2010 |
| WO | 2012024276 | | 2/2012 |

OTHER PUBLICATIONS

International Preliminary Report on Patentability and Written Opinion for International Application No. PCT/GB2013/053043 issued May 26, 2015.
International Search Report for International Application No. PCT/GB2013/053043 mailed Feb. 18, 2014.

* cited by examiner

*Primary Examiner* — Yong Chu
*Assistant Examiner* — Sonya Wright
(74) *Attorney, Agent, or Firm* — RatnerPrestia

(57) ABSTRACT

An agrochemical formulation comprising a penetrant and an agrochemical active. The penetrant is an esterified and/or etherified polyol alkoxylate obtainable by directly esterifying and/or etherifying a polyol alkoxylate. There is also provided a method of making the penetrant comprising alkoxylation of a polyol, and esterification or etherification of the formed poyol alkoxylate. The penetrant is suitable for use in agrochemical formulations to enhance penetration of the active across a leaf cuticle.

20 Claims, No Drawings

PENETRANTS FOR AGROCHEMICAL FORMULATIONS

CROSS REFERENCE TO RELATED APPLICATIONS

This application is the U.S. National Phase application of PCT International Application No. PCT/GB2013/053043, filed Nov. 19, 2013, and claims priority of GB 1220886.4, filed Nov. 20, 2012, the disclosures of which are incorporated herein by reference in their entireties for all purposes.

FIELD OF THE INVENTION

The present invention relates to esterified and/or etherified polyol alkoxylate compounds, particularly for use as penetrants, and more especially for use as penetration enhancers in agrochemical formulations comprising said compounds with one or more agrochemical actives.

BACKGROUND OF THE INVENTION

Adjuvants, and in particular penetration enhancers, are used in agrochemical formulations to aid and enhance the activity and penetration of an agrochemical active ingredient through the leaf cuticle. Adjuvants may provide improved leaf surface wetting, leaf surface penetration of the active, and do not significantly inhibit translocation of the active in the treated plant. In addition, the adjuvant should not produce unwanted phytotoxic effects on the plant.

An adjuvant is defined as a chemical or a mixture of chemicals (commonly surfactants) capable of improving the biological activity or effectiveness of an agrochemical active. Adjuvants do not themselves control or kill pests. Instead, these additives modify some property (e.g. spreading, retention, penetration, droplet size etc.) of the agrochemical formulation which improves the ability of the active to penetrate, target, or protect the target organism. The typical types of compounds used as adjuvants may include surfactants, emulsifiers, oils, and salts.

In particular, certain adjuvants (typically termed penetrants or penetration enhancers for this use) may act to specifically permit or facilitate the uptake of an agrochemical active in to a leaf. These penetrants can markedly reduce the level of the active ingredient required and they can increase the activity or extend the spectrum of effectiveness. These effects can lead to the replacement of high priced or high toxicity active ingredients by lower priced penetrants, thereby delivering better control of the target with a single product.

A number of existing penetration enhancers are known. These include ethoxylated triglycerides disclosed in US 2009/0247597 (Bayer CropScience) (Crovol CR70G). WO 2010/072341 (Cognis) discloses polyol esters which are ethoxylated and used as penetration enhancers for biocides. US 2010/0041710 (Bayer) discloses penetration enhancers of alkoxylated alkanols and also alkoxylated triglycerides. US 2008/0312290 (Bayer) discloses penetration enhancers of alkoxylated alkanols.

The existing penetrants are typically obtained by ethoxylation of naturally occurring triglycerides. As is known in the art, naturally occurring triglycerides are not pure materials but are complex mixtures, with the exact composition varying depending upon the source. There can be difficulties in the alkoxylation of complex triglycerides thereby resulting in an even more complex range of alkoxylated triglyceride products.

Therefore, there is a need for penetrants for agrochemical applications produced by a different process which enables greater reproducibility, flexibility, and control of the synthetic process enabling the production of more defined and/or purer products.

There is a growing need and desire to provide penetrants, which provide for physical properties comparable to or better than existing prior penetration enhancers. In particular, existing penetrants typically have the disadvantage that they can cover very few effects and therefore have to be carefully selected depending on the form of use and type of formulation. There is a need to provide a penetrant which can exhibit broader applicability.

The present invention also seeks to provide the use of penetrants in agrochemical compositions in combination with an agrochemical active, where the penetrant may provide comparable or improved properties (e.g. deposition characteristics, penetration levels, phytotoxicity etc.) compared to existing penetrants.

The present invention also seeks to provide the use of agrochemical concentrates and dilute formulations comprising said penetrants.

SUMMARY OF THE INVENTION

According to a first aspect of the present invention there is provided an agrochemical formulation comprising;
i) at least one penetrant; and
ii) at least one agrochemical active wherein the penetrant is an esterified and/or etherified polyol alkoxylate obtainable by directly esterifying and/or etherifying a polyol alkoxylate, where said esterified and/or etherified a polyol alkoxylate has general structure (I):

$$P.[(AO)_n-R^1]_m \qquad (I)$$

wherein:
P is the residue of a polyol, said polyol having m active hydrogen atoms, where m is an integer in the range from 2 to 9;
AO is an oxyalkylene group;
each n independently represents an integer in the range from 1 to 100;
the total of n multiplied by m is in the range from 10 to 300;
each $R^1$ independently represents hydrogen, a $C_1$ to $C_{28}$ hydrocarbyl, or an alkanoyl group represented by $-C(O)R^2$ wherein $R^2$ represents a $C_1$ to $C_{28}$ hydrocarbyl; and
wherein at least one $R^1$ group is or comprises a $C_8$ to $C_{28}$ hydrocarbyl.

Preferably, the penetrant of the first aspect may be obtained by directly esterifying and/or etherifying a polyol alkoxylate.

According to a second aspect of the present invention there is provided a method of treating vegetation to control pests, the method comprising applying an optionally diluted formulation of the first aspect either to said vegetation or to the immediate environment of said vegetation.

According to an third aspect of the present invention there is provided the use of an esterified and/or etherified polyol alkoxylate as a penetrant in an agrochemical formulation, wherein said esterified and/or etherified polyol alkoxylate is obtainable by directly esterifying and/or etherifying a polyol alkoxylate, and where said esterified and/or etherified a polyol alkoxylate has general structure (I):

$$P.[(AO)_n-R^1]_m \qquad (I)$$

wherein:

P is the residue of a polyol, said polyol having m active hydrogen atoms, where m is an integer in the range from 2 to 9;

AO is an oxyalkylene group;

each n independently represents an integer in the range from 1 to 100;

the total of n multiplied by m is in the range from 10 to 250;

each $R^1$ independently represents hydrogen, a $C_1$ to $C_{28}$ hydrocarbyl, an alkanoyl group represented by —C(O)$R^2$ wherein $R^2$ represents a $C_1$ to $C_{28}$ hydrocarbyl; and wherein at least one $R^1$ group comprises a $C_8$ to $C_{28}$ hydrocarbyl.

DETAILED DESCRIPTION

Surprisingly, it has been found that etherified and/or esterified polyol alkoxylates, formed from polyols which are first alkoxylated and subsequently esterified with fatty acids or etherified with alcohols (typically via an organohalide formed from halogenation of the alcohol), provides for penetrants having good leaf penetration properties whilst also allowing for greater reproducibility, flexibility, and control of the synthetic process. This enables the production of more defined, cleaner, and/or purer products. In particular, the desired penetrant properties may include deposition characteristics, leaf surface penetration, and phytotoxicity when used in agrochemical formulations having one or more agrochemical actives.

Existing penetrants typically have the disadvantage that they can cover very few effects and therefore have to be carefully selected depending on the form of use and type of formulation. It has now been surprisingly found that penetrants used in the agrochemical formulation of the present invention may offer better all-round performance in that they have broader applicability than typical existing penetrants.

As used herein, the terms 'for example,' 'for instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

As used herein, the term 'direct esterification' and 'direct etherification' refer to reaction of the respective carboxylic acid an alcohol (when forming an ester) or alcohol and alcohol/halide (when forming an ether). This is distinct from, and does not include, ester interchange type esterification (transesterification) or ether interchange type etherification (transetherification) reactions between an ester and another compound, such reactions characterised by an exchange of alkoxy groups or acyl groups and resulting in the formation of a different ester or ether.

It will be understood that the term 'esterified polyol alkoxylate' and 'etherified polyol alkoxylate' refers to a polyol which is first alkoxylated, and subsequently esterified or etherified.

It will be understood that, when describing the number of carbon atoms in a substituent group (e.g. '$C_1$ to $C_6$ alkyl'), the number refers to the total number of carbon atoms present in the substituent group, including any present in any branched groups. Additionally, when describing the number of carbon atoms in, for example fatty acids, this refers to the total number of carbon atoms including the one at the carboxylic acid, and any present in any branch groups.

The penetrant of the present invention are, at least notionally, built up from the group P that can be considered as the 'core group' of the compound. This core group represents the residue (i.e. after removal of m active hydrogen atoms) of a polyol containing at least m active hydrogen atoms, and is referred to herein as a polyol residue.

The term 'polyol residue' as used herein, unless otherwise defined, therefore refers to an organic radical derived from polyol by removal of m active hydrogen atoms, each hydrogen atom being from one of the hydroxyl groups present.

The term polyol is well known in the art, and refers to an alcohol comprising more than one hydroxyl group. The term 'active hydrogen' refers to the hydrogen atoms present as part of the hydroxyl groups of the polyol P. Therefore, it will be understood that the integer m, being the number of active hydrogens in said polyol, is equivalent to the number of hydroxyl groups present for each polyol.

Preferably the polyol residue is a $C_2$ to $C_{12}$ polyol residue, i.e. formed from a $C_2$ to $C_{12}$ polyol. More preferably, a $C_3$ to $C_{10}$ polyol residue, particularly $C_3$ to $C_8$ polyol residue, further preferably $C_3$ to $C_7$ polyol residue. Especially preferred are $C_5$ to $C_6$ polyol residues.

The polyol may be linear, branched, partially cyclic, or cyclic.

The index m is a measure of the alcohol functionality of the polyol, and the alkoxylation reactions will replace some or all of the active hydrogen atoms (dependant on the molar ratio of the polyol group to alkoxylation group in the reaction). It is possible that alkoxylation at a particular site may be restricted or prevented by steric hindrance.

The polyols used in the present invention have a value of m active hydrogen atoms in the range from 2 to 9. Preferably, the value of m is in the range from 2 to 8. More preferably, in the range from 3 to 7. Most preferably, in the range from 3 to 6. Especially preferred are where m represents a value of 3, 4, or 6.

As the number of hydroxyl groups present on the polyol is equivalent to the number of m active hydrogen atoms, the preferred numbers of hydroxyl groups present will be the same as listed for the preferred numbers of m active hydrogen atoms.

The polyol residue may be homogeneous in that it comprises only one specific polyol residue and is formed from one specific polyol. In an alternative embodiment, the polyol residue starting material may be heterogeneous in that it comprises a mixture of a number of different polyols have different values of m selected from those listed above, and therefore the polyol residue formed therefrom may be heterogeneous.

The polyol may be selected from diols, triols, tetrols, pentols, hexols, heptols, octols, or nonols. Preferably, the polyol may be selected from triols, tetrols, pentols, hexols, or heptols. More preferably, the polyol may be selected from triols, tetrols, or hexols.

Suitable specific polyols may be selected from ethylene glycol, isosorbide, 1,3-propanediol, trimethylolpropane, glycerol, erythritol, threitol, pentaerythritol, sorbitan, arabitol, xylitol, ribitol, fucitol, mannitol, sorbitol, galactitol, iditol, inositol, volemitol, isomalt, maltitol, or lactitol.

In one particular embodiment, polyols obtainable from natural sources may be preferred. In particular, sugar alcohols may be used to form the polyol residue. In this specification the terms 'sugars' and 'sugar alcohols' refer to a group of saccharide derived polyols having from 4 to 8 hydroxyl groups. Examples of preferred sugars and sugar alcohols may include monosaccharides and disaccharides having from 4 to 8 hydroxyl groups. Residues of monosaccharide, more preferably of glucose, fructose or sorbitol, and particularly of sorbitol or sorbitan, may be preferred as polyols obtained from natural sources.

Particularly preferred polyol residues are those wherein m represents a value of 3, 4, or 6, and where said residues are $C_5$ to $C_6$ polyol residues. Most preferably, the polyol residue is formed from trimethylolpropane, sorbitol, or sorbitan.

The oxyalkylene groups (AO) are selected from groups of the formula —($C_yH_{2y}O$)— where y is an integer selected from 2, 3, or 4. Preferably, y is an integer selected from 2 or 3.

The oxyalkylene group AO may be selected from oxyethylene, oxypropylene, oxybutylene, or oxytetramethylene. Preferably, the oxyalkylene group is selected from oxyethylene (EO) and oxypropylene (PO).

Where the oxyalkylene chain is homopolymeric, homopolymers of ethylene oxide or propylene oxide are preferred. More preferably, homopolymers of ethylene oxide are particularly preferred.

Preferably, all active hydrogen atoms present in the polyol are alkoxylated.

Where there is more than one oxyalkylene group present (i.e. where n is 2 or more) and at least two are part of the same oxyalkylene chain, the oxyalkylene groups may be the same or may be different along said oxyalkylene chain. In this embodiment, the oxyalkylene chain may be a block or random copolymer of differing oxyalkylene groups.

Preferably, where co-polymeric chains are used these are copolymers of ethylene oxide and propylene oxide. More preferably, where co-polymeric chains of ethylene oxide and propylene oxide are used, the molar proportion of ethylene oxide units comprised in the oxyalkylene chain may be at least 50%. Most preferably, the molar proportion may be at least at least 70%.

Generally, it may be preferred that the oxyalkylene chains are each homopolymeric.

The number of oxyalkylene groups in each oxyalkylene chain (i.e. the value of the each parameter n) will be in the range from 1 to 100. Preferably, in the range from 2 to 80. More preferably, in the range from 5 to 60. Further preferably, in the range from 10 to 50. Most preferably, in the range from 18 to 30.

Where polyols are used with different values of m (i.e. different numbers of hydroxyl groups) the amount of oxyalkylene groups added would be adjusted to allow for formation of oxyalkylene chains with the desired n values.

The total of the multiple of parameters n and m is in the range from 10 to 300. Preferably, in the range from 20 to 200. More preferably, in the range from 30 to 160. Further preferably, in the range from 40 to 140. Most preferably, in the range from 50 to 130.

Where the number of alkanoyl residues in the molecule is less than m, the distribution of such groups may depend on the nature of the polyol, and on the extent and effect of the alkoxylation of the polyol. Thus, where the polyol residue is derived from pentaerythritol, alkoxylation of the polyol residue may be evenly distributed over the four available sites from which active hydrogens can be removed, and on esterification or etherification the distribution of hydrocarbyl or alkanoyl groups will be close to an expected random distribution.

However, where the polyol residue is derived from compounds, such as sorbitol, where the active hydrogen atoms are not equivalent, alkoxylation may result in unequal oxyalkylene chain lengths. This may result in some chains being so short that the other (longer) chains exert significant steric effects making esterification or etherification at the 'short chain' terminal hydroxyl groups relatively difficult. In this embodiment esterification or etherification will generally preferentially take place at the 'long chain' terminal hydroxyl groups.

A polyol alkoxylate intermediate may be formed during the process of making the ethoxylated and/or etherified polyol alkoxylate. The polyol alkoxylate intermediate, which is suitable for subsequent esterification or etherification to make the penetrant, may have general structure (II):

$$P.[(AO)_n—H]_m \qquad (II)$$

wherein the values and definitions of P, AO, n, and m are as already defined according to the first aspect.

The $C_1$ to $C_{28}$ hydrocarbyl may preferably be selected from a $C_1$ to $C_{28}$ alkyl or a $C_1$ to $C_{28}$ alkenyl.

The term 'alkyl' as used herein, unless otherwise defined, refers to saturated hydrocarbon radicals being straight chain, branched, or combinations thereof, containing from 1 to 28 carbon atoms. Preferably, the alkyls each contain from 5 to 26 carbon atoms. More preferably, 10 to 24 carbon atoms. Most preferably, 16 to 22 carbon atoms.

Examples of alkyl radicals may be independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, henicosyl, docosyl, tricosyl, tetracosyl, pentacosyl, hexacosyl, heptacosyl, octacosyl, or branched variants thereof.

The alkyl radicals may preferably be selected from dodecyl, tridecyl, tetradecyl, pentadecyl, hexadecyl, heptadecyl, octadecyl, nonadecyl, eicosyl, or branched variants thereof.

The term 'alkenyl' as used herein, unless otherwise defined, refers to hydrocarbon radicals having at least one or a plurality, preferably no more than four, double bonds. The alkenyl radicals may be straight chain, or branched moieties, or combinations thereof.

The alkenyl radicals may each contain from 2 to 28 carbon atoms. Preferably, the alkenyls each contain from 5 to 26 carbon atoms. More preferably, 10 to 24 carbon atoms. Most preferably, 16 to 22 carbon atoms.

Examples of alkenyl radicals may be independently selected from ethyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenenyl henicosenyl, docosenyl, tricosenyl, tetracosenyl, pentacosenyl, hexacosenyl, heptacosenyl, octacosenyl, or branched variants thereof.

The alkyl radicals may preferably be selected from dodecenyl, tridecenyl, tetradecenyl, pentadecenyl, hexadecenyl, heptadecenyl, octadecenyl, nonadecenyl, eicosenyl, or branched variants thereof.

At least one of the $R^1$ groups present in each penetrant molecule is or comprises a $C_8$ to $C_{28}$ hydrocarbyl. Preferably, all the $R^1$ groups present in each penetrant molecule are or comprise a $C_8$ to $C_{28}$ hydrocarbyl. Where $R^1$ comprises said at least one $C_8$ to $C_{28}$ hydrocarbyl, $R^2$ will represent said at least one $C_8$ to $C_{28}$ hydrocarbyl. Preferably, all $R^1$ groups represent an alkanoyl where each $R^2$ group is a $C_8$ to $C_{28}$ hydrocarbyl.

The $C_8$ to $C_{28}$ hydrocarbyl is preferably selected from a $C_8$ to $C_{28}$ alkyl or $C_8$ to $C_{28}$ alkenyl. More preferably, a $C_{12}$ to $C_{24}$ alkyl or $C_{12}$ to $C_{24}$ alkenyl. Most preferably, a $C_{16}$ to $C_{20}$ alkyl or $C_{16}$ to $C_{20}$ alkenyl Said $C_8$ to $C_{28}$ alkyl or $C_8$ to $C_{28}$ alkenyls may be selected from the alkyl radicals and alkenyl radicals as listed herein having 8 to 28 carbon atoms.

Where said $C_8$ to $C_{28}$ hydrocarbyl is present as the $R^2$ in an alkanoyl group, said alkanoyl may preferably be a residue of a fatty acid. Preferably, each $R^1$ represents an alkanoyl group being a residue of a fatty acid.

The term 'residue of a fatty acid' as used herein refers to the moiety that is the resulting product of the fatty acid in a particular reaction scheme or subsequent formulation or chemical product, regardless of whether the moiety is actually obtained from the specified chemical species. A 'fatty acid residue' thereby refers to the moiety which results when a fatty acid participates in a particular reaction (i.e. the residue is a fatty alkanoyl group RC(O)—). The fatty acid residue is therefore 'derived' from the respective fatty acid. It is understood that this moiety can be obtained by a reaction with a species other than the specified fatty acid per se, for example, by a reaction with an unsaturated fatty acid chloride, ester, or anhydride.

The fatty acids used in the present invention are preferably selected from $C_{10}$ to $C_{30}$ fatty acids, more preferably $C_{12}$ to $C_{24}$ fatty acids, particularly $C_{14}$ to $C_{22}$ fatty acids, further preferably $C_{16}$ to $C_{20}$ fatty acids, and especially $C_{18}$ fatty acids.

The fatty acids may be selected from linear or branched fatty acids. The fatty acids may be selected from saturated or unsaturated fatty acids.

Where unsaturated fatty acids are present, these may be selected from unsaturated fatty acids comprising at least one unsaturated carbon-carbon double bond. Particularly preferred are unsaturated fatty acids having in the range from 1 to 3 carbon-carbon double bonds. Most preferred are monounsaturated fatty acids residues. The carbon-carbon double bond of the fatty chain may be present either in a cis or a trans configuration.

Preferably, the fatty acids residues used are derived from linear monounsaturated fatty acids.

Suitable saturated fatty acids may be selected from caprylic acid, capric acid, lauric acid, myristic acid, palmitic acid, stearic acid, arachidic acid, behenic acid, lignoceric acid, or cerotic acid. Preferred saturated fatty acids may be selected from lauric acid, myristic acid, palmitic acid, or stearic acid.

Suitable unsaturated fatty acids may be selected from myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, or docosahexaenoic acid. Preferred unsaturated fatty acids may be selected from oleic acid, linoleic acid, linolenic acid, palmitoleic acid, or elaidic acid. A particularly preferred unsaturated fatty acid may be oleic acid.

The fatty acids may be unsaturated fatty acid mixtures obtained from natural fats and oils, e.g. sunflower oil, soybean oil, olive oil, rapeseed oil, cottonseed oil, or tall oil.

In an alternative embodiment, the fatty acid used may be purified prior to use in the present invention.

The penetrant is obtainable by directly esterifying and/or etherifying a polyol alkoxylate. The method of making the penetrant of the first aspect comprises;
- a first step comprising alkoxylation of a polyol to form a polyol alkoxylate; and
- a second step comprising esterification or etherification of the polyol alkoxylate formed in the first step to form an esterified or etherified polyol alkoxylate.

The first step of alkoxylating the polyol may be undertaken by techniques well known in the art, for example by reacting the polyol with the required amounts of alkylene oxide, for example ethylene oxide and/or propylene oxide.

The value m is a measure of the hydroxy-functionality of the polyol, and generally the alkoxylation reactions may replace all active hydrogen atoms in the polyol. However, reaction at a particular site may be restricted or prevented by steric hindrance or suitable protection. The terminating hydroxyl groups of the polyalkylene oxide chains in the resulting compounds are then available for reaction in the second step.

The result of the first step may be an intermediate compound being polyol alkoxylate with general structure (II) as defined herein.

The second step of esterification and/or etherification of the polyol alkoxylate may be undertaken by techniques well known in the art, for example by reacting the polyol alkoxylate with a fatty acid source or alkyl radical source under acidic or basic conditions. The intermediate polyol alkoxylate therefore undergoes an esterification reaction with fatty acid, or an etherification reaction with an alkyl radical.

It can be seen that, depending on the particular reaction conditions, the alkoxylated polyol may be partially or fully esterified or etherified. At least one of the oxyalkylene chains on the polyol is esterified or etherified. Preferably, all of the oxyalkylene chains on the polyol are esterified or etherified. Most preferably, all of the oxyalkylene chains on the polyol are esterified.

In particular, it is preferred that the method of the present invention results in polyol alkoxylates in which, based on the number of hydroxyl sites present in the polyol, at least 50% are esterified and/or etherified. More preferably, the level of esterification and/or etherification is at least 60%. Further preferably, at least 70%. Most preferably, at least 80%. Esterification is preferred.

The amount of unreacted polyol present in the reaction mixture, after the first and second steps are performed, may be less than 10 wt. % of the polyol starting material. Preferably, less than 5 wt. %. More preferably, less than 2 wt. %. Further preferably, less than 1 wt. %. Most preferably, less than 0.5 wt. %.

It would be understood that unwanted side products may be formed during the process of making esterified and/or etherified polyol alkoxylate. Such side products may comprise polyol ethoxylates, (i.e. which have not been esterified and/or etherified at all) and poly oxyalkylenes (i.e. the polymers of the oxyalkylenes not bonded to a polyol or a hydrocarbyl). It has been surprisingly found that less than 10 wt. % of the reaction product is comprised of said side products.

In a suitable embodiment of the invention, on average at least 1.5 of the $R^1$ groups comprises a $C_8$ to $C_{28}$ hydrocarbyl. Preferably, on average at least 2. More preferably, at least 2.5. Said average being measured across a bulk amount of formed penetrant.

It has also been surprisingly found that, unlike existing methods, the method of making the penetrant of the present invention provides for more of the oxyalkylene starting material to comprise part of the formed polyol alkoxylate, as opposed to remaining unreacted or reacting to form side products.

Preferably, at least 50 wt. % of the oxyalkylene starting material is comprised in the formed polyol alkoxylate. More preferably, at least 60 wt. %. Further preferably, at least 70 wt. %. Most preferably, at least 80 wt. %. This feature provides for an efficient method of making the penetrant, and allows for more of the desired penetrant to be produced per unit of starting material.

Theses preferred ranges would also apply to the formed etherified and/or esterified polyol alkoxylate penetrant.

The ratio of oxyalkylene groups present in the penetrant with regard to the number active hydroxyl groups (m) is preferably in the range from 5-40:1. Preferably, 10-30:1. More preferably, 15-25:1. Most preferably, 18-22:1.

The molecular weight (weight average) of the penetrant is preferably in the range from 1,900 to 7,000, more preferably 2,200 to 5,500, particularly 2,600 to 4,500, further preferably, 3,100 to 4,100, and especially 3,500 to 4,000.

It has surprisingly been found that such a high molecular weight penetrants provide good leaf penetration properties.

As used herein, the term 'penetrant' or 'penetration enhancers' refers to a component which improves the biological action of an active compound, specifically an agrochemical active, without the component itself for its part having a biological action. In particular, the penetrant facilitates the uptake of the active compound into the leaf.

The penetrant can, for example, markedly reduce the level of the active ingredient required, and may therefore increase the activity or extend the spectrum of effectiveness. These effects can lead to the replacement of highly priced or high toxicity active ingredients by lower priced penetrants, delivering better control of the target with a single product.

Suitable penetrants may be selected from polyoxyethylene (20) trimethylolpropane monooleate, polyoxyethylene (44) trimethylolpropane monooleate, polyoxyethylene (54) trimethylolpropane monooleate, polyoxyethylene (64) trimethylolpropane monooleate, polyoxyethylene (74) trimethylolpropane monooleate, polyoxyethylene (84) trimethylolpropane monooleate, polyoxyethylene (20) trimethylolpropane dioleate, polyoxyethylene (44) trimethylolpropane dioleate, polyoxyethylene (54) trimethylolpropane dioleate, polyoxyethylene (64) trimethylolpropane dioleate, polyoxyethylene (74) trimethylolpropane dioleate, polyoxyethylene (84) trimethylolpropane dioleate, polyoxyethylene (20) trimethylolpropane trioleate, polyoxyethylene (44) trimethylolpropane trioleate, polyoxyethylene (54) trimethylolpropane trioleate, polyoxyethylene (64) trimethylolpropane trioleate, polyoxyethylene (74) trimethylolpropane trioleate, polyoxyethylene (84) trimethylolpropane trioleate, polyoxyethylene (40) sorbitan monooleate, polyoxyethylene (50) sorbitan monooleate, polyoxyethylene (65) sorbitan monooleate, polyoxyethylene (40) sorbitan monolaurate, polyoxyethylene (50) sorbitan monolaurate, polyoxyethylene (65) sorbitan monolaurate, polyoxyethylene (40) sorbitol hexaoleate, polyoxyethylene (50) sorbitol hexaoleate, or polyoxyethylene (65) sorbitol hexaoleate.

Preferably, specific penetrants may be selected from polyoxyethylene (64) trimethylolpropane trioleate, polyoxyethylene (40) sorbitol hexaoleate, polyoxyethylene (50) sorbitol hexaoleate, polyoxyethylene (40) sorbitan monooleate, polyoxyethylene (50) sorbitan monooleate, or polyoxyethylene (65) sorbitan monooleate.

Most preferably, the penetrant may be selected from polyoxyethylene (64) trimethylolpropane trioleate, polyoxyethylene (40) sorbitol hexaoleate, or polyoxyethylene (50) sorbitol hexaoleate.

Agrochemically active compounds, in particular systemic insecticides and fungicides, require a formulation which allows the active compounds to be taken up by the plant/the target organisms.

The penetrant may be combined with other components in order to form an agrochemical formulation comprising at least one agrochemical active.

Accordingly, agrochemical active compounds may be formulated as an emulsifiable concentrate (EC), emulsion concentrate (EW), suspension concentrate (SC), soluble liquid (SL), as an oil-based suspension concentrate (OD), and/or suspoemulsions (SE).

In an EC formulation and in an SL formulation, the active compound may be present in dissolved form, whereas in an OD or SC formulation the active compound may be present as a solid.

It is envisaged that the penetrant of the present invention will particularly find use in a SC formulation. Typically, said SC formulation may be in the form of an aqueous solution with the penetrant dissolved therein, and an insoluble solid agrochemical active dispersed in said solution.

The term 'agrochemical formulation' as used herein refers to compositions including an active agrochemical, and is intended to include all forms of compositions, including concentrates and spray formulations. The agrochemical formulation of the present invention may be in the form of a concentrate, a diluted concentrate, or a sprayable formulation.

Agrochemical concentrates are agrochemical compositions, which may be aqueous or non-aqueous, which are designed to be diluted with water (or a water based liquid) to form the corresponding spray formulations. Said compositions include those in liquid form (such as solutions, emulsions, or dispersions) and in solid form (especially in water dispersible solid form) such as granules or powders.

Spray formulations are aqueous agrochemical formulations including all the components which it is desired to apply to the plants or their environment. Spray formulations can be made up by simple dilution of concentrates containing desired components (other than water), or by mixing of the individual components, or a combination of diluting a concentrate and adding further individual components or mixtures of components. Typically such end use mixing is carried out in the tank from which the formulation is sprayed, or alternatively in a holding tank for filling the spray tank. Such mixing and mixtures are typically termed tank mixing and tank mixtures.

A penetrant may therefore be incorporated into the formulation of the agrochemical active compound (in-can formulation) or be added after dilution of the concentrated formulation of the spray liquor (tank-mix). To avoid dosage errors and to improve user safety during application of agrochemical products, it is advantageous to incorporate the penetrants into the formulation. This also avoids the unnecessary use of additional packaging material for the tank-mix products.

According to the needs of the customer, concentrates thus formed may comprise typically up to 95 wt. % agrochemical actives. Said concentrates may be diluted for use resulting in a dilute composition having an agrochemical active concentration of about 0.5 wt. % to about 1 wt. %. In said dilute composition (for example, a spray formulation, where a spray application rate may be from 10 to 500 l·ha$^{-1}$) the agrochemical active concentration may be in the range from about 0.001 wt. % to about 1 wt. % of the total formulation.

The penetrant of the formula (I) will typically be used in an amount in proportion to the amount of the active agrochemical. In agrochemical formulation concentrates, the proportion of penetrant will depend on the solubility of the components in the liquid carrier. Typically, the concentration of penetrant or penetrants in such a concentrate will be from 1 wt. % to 99 wt. %. Preferably, from 1 wt. % to 70 wt. %. More preferably, from 3 wt. % to 50 wt. %. Further preferably, from 5 wt. % to 30 wt. %. Most preferably, from 7 wt. % to 20 wt. %.

Upon dilution to form, for example, a spray formulation, the penetrant will typically be present at a concentration of from 0.01 wt. % to 2 wt. %, more usually from 0.03 wt. % to 0.5 wt. % of the spray formulation.

The ratio of penetrant to active agrochemical in the agrochemical formulation is preferably from about 0.1:1 to about 1:1. More preferably, from about 0.3:1 to about 0.8:1. This ratio range will generally be maintained for concentrate forms of formulations e.g. where the penetrant is included in a dispersible liquid concentrate or dispersible solid granule formulation, and in spray formulations. However, in using such concentrates, it is possible to add further components in tank mixing.

When concentrates (solid or liquid) are used as the source of active agrochemical and/or penetrant, the concentrates will typically be diluted to form the spray formulations. The dilution may be with from 50 to 10,000, particularly 100 to 1,000, times the total weight of the concentrate of water to form the spray formulation.

Where the agrochemical active is present in the aqueous end use formulation as solid particles, most usually it will be present as particles mainly of active agrochemical. However, if desired, the active agrochemical can be supported on a solid carrier.

Where the dispersed phase is a non-aqueous liquid, it will typically be an oil. The oil may be or include a mineral oil, including aliphatic (paraffin) mineral oils and aromatic mineral or synthetic oils, such as those sold under the trade name Solvesso; an optionally hydrogenated vegetable oil, such as an optionally hydrogenated cotton seed oil, linseed oil, mustard oil, neem oil, niger seed oil, oiticica oil, olive oil, palm oil, palm kernel oil, peanut oil, perilla oil, poppy seed oil, rape seed oil, safflower oil, sesame oil, or soybean oil; an ester oil (a synthetic ester oil), especially a $C_{16}$ ester of a $C_8$ to $C_{22}$ fatty acid, especially a $C_{12}$ to $C_{18}$ fatty acid, or a mixture of esters, such as methyl laurate, 2-ethylhexyl laurate, heptadecanoate, heptadecenoate, heptadecadienoate, stearate or oleate, and in particular methyl laurate and oleate; N-methylpyrrolidone; or an isoparaffin; or a mixture of such oils.

The spray formulations will typically have a pH within the range from moderately acid e.g. about 3 to moderately alkaline e.g. about 10, and particular near neutrality, for example 6 to 8. More concentrated formulations will have similar degrees of acidity/alkalinity, but as they may be largely non-aqueous, pH is not necessarily an appropriate measure of this.

The agrochemical formulation may include solvents (other than water) such as monopropylene glycol, oils which can be vegetable or mineral oils such as spray oils (oils included in spray formulations as non-surfactant adjuvants), associated with the penetrant. Such solvents may be included as a solvent for the penetrant and/or as a humectant e.g. especially propylene glycol. When used such solvents will typically be included in an amount of from 5 wt. % to 500 wt. %, desirably 10 wt. % to 100 wt. %, by weight of the penetrant. Such combinations can also include salts such as ammonium chloride and/or sodium benzoate and or urea especially as gel inhibition aids.

The agrochemical formulation may also include preservatives and/or anti-microbials such as organic acids or their esters or salts such as ascorbic e.g. ascorbyl palmitate, sorbic e.g. potassium sorbate, benzoic e.g. benzoic acid and methyl and propyl 4-hydroxybenzoate, propionic e.g. sodium propionate, phenol e.g. sodium 2-phenylphenate; 1,2-benzisothiazolin-3-one; or formaldehyde as such or as paraformaldehyde; or inorganic materials such as sulphurous acid and its salts, typically in amounts of 0.01 wt. % to 1 wt. % of the composition and/or antifoam agents e.g. polysiloxane antifoam agents, typically in amounts of 0.005 wt. % to 1 wt. % of the composition.

Other adjuvants, particularly surfactant adjuvants, may be included in the compositions and formulations of and used in this invention. Examples include linear alcohol alkoxylates (as may be present in materials made for use in this invention derived from linear alcohols in the starting materials); alkylpolysaccharides (more properly called alkyl oligosaccharides); fatty amine ethoxylates e.g. coconut alkyl amine 2EO; sorbitan and sorbitol ethoxylate derivatives, such as those sold under the trade names Atlox and Tween by Croda Europe Limited; and derivatives of alk(en)yl succinic anhydride, in particular those described in PCT applications WO 94/00508 and WO 96/16930.

The agrochemical formulations may also include other components including:

- binders, particularly binders which are readily water soluble to give low viscosity solutions at high binder concentrations, such as polyvinylpyrrolidone; polyvinyl alcohol; carboxymethyl cellulose; gum arabic; sugars e.g. sucrose or sorbitol; starch; ethylene-vinyl acetate copolymers, sucrose and alginates,
- diluents, absorbents or carriers such as carbon black; talc; diatomaceous earth; kaolin; aluminium, calcium or magnesium stearate; sodium tripolyphosphate; sodium tetraborate; sodium sulphate; sodium, aluminium and mixed sodium-aluminium silicates; and sodium benzoate,
- disintegration agents, such as surfactants, materials that swell in water, for example carboxy methylcellulose, collodion, polyvinylpyrrolidone and microcrystalline cellulose swelling agents; salts such as sodium or potassium acetate, sodium carbonate, bicarbonate or sesquicarbonate, ammonium sulphate and dipotassium hydrogen phosphate;
- wetting agents such as alcohol ethoxylate and alcohol ethoxylate/propoxylate wetting agents;
- dispersants such as sulphonated naphthalene formaldehyde condensates and acrylic copolymers such as the comb copolymer having capped polyethylene glycol side chains on a polyacrylic backbone;
- emulsifiers such as alcohol ethoxylates, ABA block co polymers, or castor oil ethoxylates;
- antifoam agents, typically at a concentration of from 1 to 10% by weight of the granule; and
- viscosity modifiers such as commercially available water soluble or miscible gums, e.g. xanthan gums, and/or cellulosics, e.g. carboxy-methyl, ethyl or propylcellulose.

The invention accordingly includes a spray formulation including at least one dispersed solid phase agrochemical active, and as a penetrant. The spray formulation of the invention may be made by dilution of a concentrate as described above.

The invention further includes a method of treating plants using spray formulations including at least one dispersed phase agrochemical and a penetrant of the first aspect. The agrochemical may be one or more phytoactives, for example growth regulators and/or herbicides, and/or pesticides, for example insecticides, fungicides or acaricides.

Accordingly the invention further includes method of use including:

- a method of killing or inhibiting vegetation by applying to the vegetation, or the immediate environment of the vegetation e.g. the soil around the vegetation, a spray formulation including at least one dispersed phase agrochemical and a penetrant of the first aspect; and a method of killing or inhibiting pests of plants by applying to the plants or the immediate environment of the plants e.g. the soil around the plants, a spray formulations including at least one dispersed phase agrochemical which is one or more pesticides, for example insecticides, fungicides or acaricides, and a penetrant of the first aspect.

Suitable agrochemical actives for use in the formulations according to the invention are all agrochemically active compounds, preferably those which are solid at room temperature. It is envisaged that the penetrant of the present invention would have broad applicability to all types of agrochemical actives.

Agrochemical actives refer to biocides which, in the context of the present invention, are plant protection agents, more particular chemical substances capable of killing different forms of living organisms used in fields such as medicine, agriculture, forestry, and mosquito control. Also counted under the group of biocides are so-called plant growth regulators.

Biocides for use in agrochemical formulations of the present invention are typically divided into two sub-groups:
pesticides, including fungicides, herbicides, insecticides, algicides, moluscicides, miticides and rodenticides, and
antimicrobials, including germicides, antibiotics, antibacterials, antivirals, antifungals, antiprotozoals and antiparasites.

In particular, biocides selected from insecticides, fungicides, or herbicides may be particularly preferred.

Pesticides

The term 'pesticide' will be understood to refer to any substance or mixture of substances intended for preventing, destroying, repelling, or mitigating any pest. A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given.

A fungicide is a chemical control of fungi. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies.

Examples for suitable fungicides, according to the present invention, encompass the following species: (3-ethoxypropyl)mercury bromide, 2-methoxyethylmercury chloride, 2-phenylphenol, 8-hydroxyquinoline sulphate, 8-phenylmercuri oxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulphide, benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulphide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper (II) carbonate, basic, copper fungicides, copper hydroxide, copper naphthenate, copper oleate, copper oxychloride, copper(II) sulphate, copper sulphate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulphon, dinoterbon, diphenylamine, dipyrithione, disulphiram, ditalimfos, dithianon, dithiocarbamate fungicides, DNOC, dodemorph, dodicin, dodine, DONATODINE, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulph, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, fluopicolide, fluoroimide, fluotrimazole, fluoxastrobin, fluquinconazole, flusilazole, flusulphamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulphocarb, methfuroxam, methyl bromide, methyl isothiocyanate, methylmercury benzoate, methylmercury dicyandiamide, methylmercury pentachlorophenoxide, metiram, metominostrobin, metrafenone, metsulphovax, milneb, morpholine fungicides, myclobutanil, myclozolin, N-(ethylmercury)-p-toluenesulphonanilide, nabam, natamycin, nitrostyrene, nitrothal-isopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulphamide fungicides, phosdiphen, phthalide, phthalimide fungicides, picoxystrobin, piperalin, polycarbamate, polymeric dithiocarbamate fungicides, polyoxins, polyoxorim, polysulphide fungicides, potassium azide, potassium polysulphide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfiir, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulphide, spiroxamine, streptomycin, strobilurin fungicides, sulphonanilide fungicides, sulphur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide, and mixtures thereof.

An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are non-selective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat.

Suitable herbicides may be selected from the group comprising: aryloxycarboxylic acid e.g. MCPA, aryloxyphenoxypropionates e.g. clodinafop, cyclohexanedione oximes e.g. sethoxydim, dinitroanilines e.g. trifluralin, diphenyl ethers e.g. oxyfluorfen, hydroxybenzonitriles e.g. bromoxynil, sulphonylureas e.g. nicosulphuron, triazolopyrimidines e.g. penoxsulam, triketiones e.g. mesotriones, or ureas e.g. diuron.

Particularly preferred herbicides may be selected from 2,4-dichlorophenoxyacetic acid (2,4-D), atrazine, dicamba as benzoic acid, glyphosate, imazapic as imidazolinone, metolachlor as chloroacetamide, picloram, clopyralid, and triclopyr as pyridinecarboxylic acids or synthetic auxins.

An insecticide is a pesticide used against insects in all developmental forms, and include ovicides and larvicides used against the eggs and larvae of insects. Insecticides are used in agriculture, medicine, industry and the household.

Suitable insecticides may include those selected from:
Chlorinated insecticides such as, for example, Camphechlor, DDT, Hexachloro-cyclohexane, gamma-Hexachlorocyclohexane, Methoxychlor, Pentachlorophenol, TDE, Aldrin, Chlordane, Chlordecone, Dieldrin, Endosulphan, Endrin, Heptachlor, Mirex and their mixtures;

Organophosphorous compounds such as, for example, Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulphoton, Ethoprop, Fenamiphos, Fenitrothion, Fenthion, Fosthiazate, Malathion, Methamidophos, Methidathion, Methyl-parathion, Mevinphos, Naled, Omethoate, Oxydemeton-methyl, Parathion, Phorate, Phosalone, Phosmet, Phostebupirim, Pirimiphos-methyl, Profenofos, Terbufos, Tetrachlorvinphos, Tribufos, Trichlorfon and their mixture;

Carbamates such as, for example, Aldicarb, Carbofuran, Carbaryl, Methomyl, 2-(1-Methylpropyl)phenyl methylcarbamate and their mixtures;

Pyrethroids such as, for example, Allethrin, Bifenthrin, Deltamethrin, Permethrin, Resmethrin, Sumithrin, Tetramethrin, Tralomethrin, Transfluthrin and their mixtures;

Plant toxin derived compounds such as, for example, Denis (rotenone), Pyrethrum, Neem (Azadirachtin), Nicotine, Caffeine and their mixtures.

Neonicotinoids such as imidacloprid.

Abamectin e.g. emamectin

Oxadiazines such as indoxacarb

Anthranilic diamides such as rynaxypyr

Rodenticides are a category of pest control chemicals intended to kill rodents. Suitable rodenticides may include anticoagulants, metal phosphides, phosphides, and calciferols (vitamins D), and derivatives thereof.

Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulphate. A nematicide is a type of chemical pesticide used to kill parasitic nematodes (a phylum of worm).

Antimicrobials

In the following examples, antimicrobials suitable for agrochemical compositions according to the present invention are given.

Bactericidal disinfectants may include those selected from active chlorines, active oxygen, iodine, concentrated alcohols, phenolic substances, cationic surfactants, strong oxidisers, heavy metals and their salts, and concentrated strong acids and alkalis between pH of from 1 to 13.

Suitable antiseptics (i.e., germicide agents that can be used on human or animal body, skin, mucoses, wounds and the like) may include diluted chlorine preparations, iodine preparations, peroxides, alcohols with or without antiseptic additives, weak organic acids, phenolic compounds, and cation-active compounds.

Preferred actives are those with systemic or partially systemic mode of action.

Particular preference is given to active compounds from the classes of the azole fungicides (azaconazole, bitertanol, bromuconazole, cyproconazole, diclobutrazole, difenoconazole, diniconazole, diniconazole-M, epoxiconazole, etaconazole, fenarimol, fenbuconazole, fluquinconazole, flurprimidol, flusilazole, flutriafol, furconazole, furconazole-cis, hexaconazole, imazalil, imazalil sulphate, imibenconazole, ipconazole, metconazole, myclobutanil, nuarimol, oxpoconazole, paclobutrazole, penconazole, pefurazoate, prochloraz, propiconazole, prothioconazole, pyrifenox, simeconazole, tebuconazole, tetraconazole, triadimefon, triadimenol, triflumizole, triforin, triticonazole, uniconazole, voriconazole, viniconazole), strobilurin fungicides (azoxystrobin, dimoxystrobin, fluoxastrobin, kresoxim-methyl, metominostrobin, orysastrobin, picoxystrobin, pyraclostrobin, trifloxystrobin), the SDH fungicides, the chloronicotinyl insecticides (clothianidin, dinotefuran, imidacloprid, thiamethoxam, nitenpyram, nithiazin, acetamiprid, nitenpyram, thiacloprid), the insecticidal ketoenols (spirodiclofen, spiromesifen, spirotetramate), fiproles (fiprole, ethiprole) and butenolides, and also pymetrozine, fluopicolid, N-(3',4'-dichloro-5-fluoro-1,1'-biphenyl-2-yl)-3-(difluoromethyl)-1-methyl-1H-pyrazole-4-carboxamide and N-[2-[3-chloro-5-(trifluoromethyl)-2-pyridinyl]ethyl]-2-(trifluoromethyl)benzamide. Particular preference is also given to herbicides, in particular sulphonylureas, triketones and herbicidal ketoenols, and also safeners.

Very particularly preferred as active compounds are;
the fungicides tebuconazole, prothioconazole, N-(3',4'-dichloro-5-fluoro-1,1'-biphenyl-2-yl)-3-(difluoromethyl)-1-methyl-1H-pyrazole-4-carboxamide (known from WO 03/070705), N-[2-[3-chloro-5-(trifluoromethyl)-2-pyridinyl]ethyl]-2-(trifluoromethyl)benzamide (known from WO 04/16088), trifloxystrobin, fluopicolid;
the insecticides imidacloprid, thiamethoxam, clothianidin, thiacloprid, spirotetramate, fipronil, ethiprol and
the herbicides thiencarbazone, sulcotrione, mesotrione, tembotrione, pyrasulphotole, iodosulphuron, mesosulphuron and forarnsulphuron.

The penetrant of the present invention, when used in an agrochemical formulation, provides desired effects, in particular for good leaf penetration, low phytotoxicity, and good deposition.

Leaf penetration enhancers provide help to spread an agrochemical active across the leaf and penetrate the leaf surface by promoting passage of the active across the leaf surface.

Penetrants can cause undesired phytotoxic effects. Phytotoxicity can be described as damage to a plant and it is well known that existing penetrants can facilitate this damage.

All of the features described herein may be combined with any of the above aspects, in any combination.

In order that the present invention may be more readily understood, reference will now be made, by way of example, to the following description.

It will be understood that all tests and physical properties listed have been determined at atmospheric pressure and room temperature (i.e. 20° C.), unless otherwise stated herein, or unless otherwise stated in the referenced test methods and procedures.

Synthesis of Penetrant (P4)

A two-step synthesis route was used to form penetrant P4. Trimethylolpropane was used as the polyol, although use of other polyols is of course possible. The trimethylolpropane was first alkoxylated using a condensation reaction of trimethylolpropane with epoxides.

The resulting polyoxyethylene (64) trimethylolpropane was esterified with the oleic fatty acid. A natural fatty acid mixture derived from rape seed oil (i.e. high in oleic acid) was used.

The fatty acid mixture and the ethoxylated trimethylolpropane were preheated overnight to a temperature of 60° C. The heated mixture was agitating to ensure homogeneity p-Toluenesulphonic acid was then added to the heated mixture under nitrogen whilst heating to 220° C. with agitation. The reaction was monitored by measuring the acid value at regular intervals and was deemed to be complete when no change was observed between measurements (typically around 5 mg KOH/g).

Polyoxyethylene (64) trimethylolpropane trioleate (P4) was yielded. It can be seen that other penetrants as listed in Table 1 would also be producible by the same synthetic scheme. All penetrants made are shown in Table 1.

TABLE 1

Synthesised penetrants

| Compound Number | Mono-(M), Di-(D) Tri-(T) ester | Level of Ethoxylation (moles per molecule) |
| --- | --- | --- |
| P1 | M | 20 |
| P2 | M | 44 |
| P3 | M | 54 |
| P4 | M | 64 |
| P5 | M | 84 |
| P6 | D | 20 |
| P7 | D | 44 |
| P8 | D | 54 |
| P9 | D | 64 |
| P10 | D | 84 |
| P11 | T | 20 |
| P12 | T | 44 |
| P13 | T | 54 |
| P14 | T | 64 |

Reaction times for forming mono-esters and di-esters were typically around 3-4 hours at 220° C., reaching acid values of <5 mg KOH/g in this time. The hydroxyl values of the mono- and di-esters were in line with expected values. The tri-esters required 6-8 hours at 220° C. to reach an acid value of <8 mg KOH/g. Saponification values of all the materials produced were concurrent with theoretical values.

The synthesised compounds P1 to P14 were then used in experiments, as detailed below, to demonstrate penetrant activity and other properties.

Leaf Penetration Examples

The following test method was used to assess leaf penetration properties of the synthesised ethoxylated polyol alkoxylates P1 to P18.

Franz cells were set up containing:
Receptor solution: 10 mM sodium phosphate buffer pH 6.0 containing 0.1 mM sodium azide
Donor solution: unformulated pesticide containing 0.5 g/l of Imidacloprid (N-[1-[(6-Chloro-3-pyridyl)methyl]-4,5-dihydroimidazol-2-yl]nitramide) and 2.5 g/l of penetrant, in 5 mM lactic acid (pre-buffered with KOH), preserved with 0.5 mM sodium azide, (+/−0.25% w/v), i.e. 2.5 g/l donor).

The Franz cell experiments were used for diffusion experiments. Isolated cuticles from apple leaves (Malus domestica cv. 'Golden Delicious') were prepared based on the method detailed in US 2009/0247597. The donor compartment was removed to aid deposit formation. Experiments were performed at a controlled temperature of 20° C., and a controlled relative humidity of 58%. A calibration was carried out (0-100% penetration) obtaining the concentration of Imidacloprid in the receiver solution removed from the Franz Cell.

HPLC-UV was used to assay imidacloprid concentration using an Agilent 1260 Quaternary LC system. Each penetrant was tested for leaf penetration properties, with a total of 18 Franz cells used for percentage penetration determination. A calibration was carried out before each set of samples was analysed.

Suspension Concentrate Formulation

Suspension concentrate formulations comprising the penetrants were formed. Polymeric surfactants (Atlox 4913 and Atlas G-5002L, both sold by Croda Europe Limited), water and Imidacloprid insecticide were homogenised. The millbase was milled (Eiger-Torrance mini mill, 3,500 rpm for 15 minutes). After discharge from the mill, xanthan gum thickener, glycerol antifreeze, and penetrant were added with stirring. The suspension concentration formulations used are shown in Table 2.

TABLE 2

Suspension concentrate formulation composition

| Component | Weight/g | Wt. % |
|---|---|---|
| Imidacloprid | 18.7 | 17.22 |
| Atlox 4913 | 4.0 | 3.68 |
| Atlas G-5002L | 0.6 | 0.55 |
| Xanthan gum | 0.6 | 0.55 |
| Glycerol | 10.0 | 9.21 |
| Penetrant | 10.0 | 9.21 |
| Water | 64.72 | 59.58 |
| Total | 108.62 | 100 |

The penetration of Imidacloprid through apple leaf cuticles was measured after 72 hours, and the results shown in Table 3.

TABLE 3

Uptake of Imidacloprid results for penetrants

| Penetrant | % Penetration after 72 hours* |
|---|---|
| P1 | 13.9 |
| P2 | 12.6 |
| P3 | 15.8 |
| P4 | 13.1 |
| P6 | 13.9 |
| P7 | 15.2 |
| P8 | 15.4 |
| P9 | 17.8 |
| P10 | 14.5 |
| P12 | 12.4 |
| P13 | 9.8 |
| P14 | 10.9 |
| P15 | 13.6 |
| P16 | 18.7 |

*Mean average value from 18 repetitions for penetration through apple leaf cuticles (T = 20° C., RH = 58%)

The penetration of Imidacloprid through apple leaf cuticles after 72 hours was enhanced by all the penetrants as shown in Table 3. All the penetrants tested therefore enhanced the penetration of Imidacloprid significantly compared to use of the active alone which gave a value of 1.7% penetration after 72 hours.

Deposition Analysis Examples

A formulation having the same composition as shown in Table 2 was formed. Atlox 4913, Atlas G-5002L, water, and Imidacloprid were mixed together and ultraturraxed at 10,000 rpm for 1 minute. This mix was then milled using an Eiger-Torrance mini mill at 3,500 rpm for 15 minutes. The milled material was discharged into a tared beaker and the appropriate pro rata quantity of xanthan gum, glycerol, and penetrant mixture was added. The formulation was then subjected to high shearing at 10,000 rpm using an ultraturrax for 1 minute.

The formulation was subjected to a 1/200 dilution with 342 ppm $Ca^{2+}$ hard water to replicate the concentration representative the formulation sprayed in the field. A 20 µl droplet of each diluted formulation was placed on an individual adaxial cuticle membranes isolated from apple (Malus domestica 'Golden Delicious') leaves.

The deposit formed, upon evaporation of water, within a droplet penetrant-containing formulation was evaluated using Scanning Electron Microscopy (SEM) to assess the deposit pattern on adaxial cuticular membranes isolated from apple (Malus domestica 'Golden Delicious') leaves. The cuticles were coated with gold (for conducting purposes) using a sputtering method and images were obtained using a FEI Quanta 200. The voltage applied was 5 kV which was low enough to provide good resolution without damaging to the cuticles.

Typically needle-like crystals form when existing penetrants are used. These pesticide needles may vary in length from about 20 µm up to 170 µm, and typical pore channel width is about 30 µm.

Microscopy analysis of the penetrants tested showed crystals measuring in the range of 5-7 µm that were homogeneously distributed (i.e. no 'coffee-ring' structure formed) and small enough to have enhanced bioavailability. Most of the pesticide was therefore seen sitting inside of the pore channels which indicates an improved bioavailability. The results indicate an increase in penetration of Imidacloprid using the penetrants.

Phytotoxicity Analysis Examples

Healthy, well-established poinsettia plants were obtained. The treatment droplets for all testing included the insecticide Imidacloprid (0.04% w/w, 0.4 g/L) and penetrant (0.10%, 1.0 g/L). The droplet application test for each bract to assess any phytotoxicity was six 10 µL droplets applied to the upper side of the bract. Results are shown in Table 4.

TABLE 4

Phytotoxicity for penetrants

| Penetrant | 1 Day After Treatment | 6 Days After Treatment |
|---|---|---|
| P1 | 0 | 0 |
| P2 | 0 | 0 |
| P3 | 0 | 0 |
| P4 | 0 | 0 |
| P6 | 0 | 0 |
| P8 | 0 | 0 |
| P9 | 0 | 0 |
| P10 | 0 | 0 |
| P12 | 0 | 0 |
| P14 | 0 | 0 |
| P15 | 0 | 0 |
| P16 | 0 | 0 |

Evaluation of phytotoxicity was based on giving values regarding observed necrosis, where 0=no necrosis; 1=slight spot-like necrosis on the bract area wetted by the drop; 2=ring shaped necrosis; 3=extended necrosis.

The phytotoxicity results obtained showed that all penetrants tested did not exhibit any phytotoxicity.

It is to be understood that the invention is not to be limited to the details of the above embodiments, which are described by way of example only. Many variations are possible.

The invention claimed is:

1. An agrochemical formulation comprising;
   i) at least one penetrant; and
   ii) at least one agrochemical active;
wherein the penetrant is an esterified and/or etherified polyol alkoxylate obtainable by directly esterifying and/or etherifying a polyol alkoxylate, where said esterified and/or etherified a polyol alkoxylate has general structure (I):

$$P.[(AO)_n-R^1]_m \qquad (I)$$

wherein:
   P is a residue of a polyol, said polyol having m active hydrogen atoms, where m is an integer in the range from 2 to 9;
   AO is an oxyalkylene group;
   each n independently represents an integer in the range from 1 to 100;
   the total of n multiplied by m is in the range from 30 to 160;
   each $R^1$ independently represents hydrogen, a $C_1$ to $C_{28}$ hydrocarbyl, or an alkanoyl group represented by $-C(O)R^2$ wherein $R^2$ represents a $C_1$ to $C_{28}$ hydrocarbyl; and
   wherein at least one $R^1$ group is or comprises a $C_8$ to $C_{28}$ hydrocarbyl.

2. The formulation according to claim 1, wherein the polyol residue is a $C_2$ to $C_{12}$ polyol residue.

3. The formulation according to claim 1, wherein the value of m active hydrogen atoms is in the range from 3 to 7.

4. The formulation according to claim 1, wherein the polyol is selected from ethylene glycol, isosorbide, 1,3-propanediol, trimethylolpropane, glycerol, erythritol, threitol, pentaerythritol, sorbitan, arabitol, xylitol, ribitol, fucitol, mannitol, sorbitol, galactitol, iditol, inositol, volemitol, isomalt, maltitol, or lactitol.

5. The formulation according to claim 4, wherein the polyol is selected from trimethylolpropane, sorbitol, or sorbitan.

6. The formulation according to claim 1, wherein the oxyalkylene group AO is selected from oxyethylene, oxypropylene, oxybutylene, or oxytetramethylene.

7. The formulation according to claim 1, wherein the number of oxyalkylene groups in each oxyalkylene chain is in the range from 2 to 80.

8. The formulation according to claim 1, wherein the total of the multiple of parameters n and m is in the range from 10 to 25040 to 140.

9. The formulation according to claim 1, wherein the $C_1$ to $C_{28}$ hydrocarbyl is selected from a $C_1$ to $C_{28}$ alkyl or a $C_1$ to $C_{28}$ alkenyl.

10. The formulation according to claim 1, wherein all the $R^1$ groups present in each penetrant molecule are or comprise a $C_8$ to $C_{28}$ hydrocarbyl.

11. The formulation according to claim 10, wherein each $R^1$ represents an alkanoyl group being a residue of a fatty acid.

12. The formulation according to claim 11, wherein the fatty acids are selected from $C_{10}$ to $C_{30}$ fatty acids.

13. The formulation according to claim 11, wherein the fatty acid is selected from myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, or docosahexaenoic acid.

14. The formulation according to claim 1, wherein the ratio of oxyalkylene groups present in the penetrant with regard to the number active hydroxyl groups (m) is in the range from 5-40:1.

15. The formulation according to claim 1, wherein the molecular weight (weight average) of the penetrant is in the range from 1,900 to 7,000.

16. The formulation according to claim 1, wherein the penetrant is selected from polyoxyethylene (64) trimethylolpropane trioleate, polyoxyethylene (40) sorbitol hexaoleate, polyoxyethylene (50) sorbitol hexaoleate, polyoxyethylene (40) sorbitan monooleate, polyoxyethylene (50) sorbitan monooleate, or polyoxyethylene (65) sorbitan monooleate.

17. The formulation according to claim 1, wherein the penetrant is obtained by directly esterifying and/or etherifying a polyol alkoxylate.

18. The formulation according to claim 1, wherein the formulation is in the form of an emulsifiable concentrate (EC), emulsion concentrate (EW), suspension concentrate (SC), soluble liquid (SL), as an oil-based suspension concentrate (OD), and/or suspoemulsions (SE).

19. The formulation according to claim 1, wherein the ratio of penetrant to active agrochemical in the agrochemical formulation is from about 0.1:1 to about 1:1.

20. A method of treating vegetation to control pests, the method comprising applying an optionally diluted formulation in accordance with claim 1, either to said vegetation or to an immediate environment of said vegetation.

* * * * *

UNITED STATES PATENT AND TRADEMARK OFFICE
CERTIFICATE OF CORRECTION

PATENT NO. : 9,681,658 B2
APPLICATION NO. : 14/443865
DATED : June 20, 2017
INVENTOR(S) : Trevor Graham Blease et al.

It is certified that error appears in the above-identified patent and that said Letters Patent is hereby corrected as shown below:

In the Claims

At Column 21, Lines 7 and 8 of the Letters Patent, in Claim 1, "where said esterified and/or etherified a polyol alkoxylate" should read --where said esterified and/or etherified polyol alkoxylate--.

At Column 21, Line 48 of the Letters Patent, in Claim 8, "10 to 25040 to 140" should read --40 to 140--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*